United States Patent [19]

Harper

[11] 4,042,372
[45] Aug. 16, 1977

[54] SUBSTITUTED THIADIAZOLOTRIAZINEDIONES AND METHOD OF PREPARATION

[75] Inventor: Richard W. Harper, Indianapolis, Ind.

[73] Assignee: Eli Lilly and Company, Indianapolis, Ind.

[21] Appl. No.: 743,439

[22] Filed: Nov. 19, 1976

[51] Int. Cl.$^2$ .................... C07D 513/04; A01N 9/12
[52] U.S. Cl. ..................... 71/90; 544/113; 544/223
[58] Field of Search ................ 260/248 NS, 247.1 L; 71/90

[56] References Cited

PUBLICATIONS

Goburn et al., *J. Org. Chem.*, vol. 38, pp. 3868–3871 (1973).

*Primary Examiner*—John M. Ford
*Attorney, Agent, or Firm*—Dwight E. Morrison; Arthur R. Whale

[57] ABSTRACT

Novel substituted thiadiazolotriazinediones, active as herbicides, antimicrobial agents, antiviral agents, and a method for their preparation, together with herbicidal methods and compositions employing said novel compounds.

12 Claims, No Drawings

SUBSTITUTED THIADIAZOLOTRIAZINEDIONES AND METHOD OF PREPARATION

BACKGROUND OF THE INVENTION

1. Field of the Invention

This invention relates to substituted thiadiazolotriazinediones active as herbicides, as antimicrobial and antiviral agents, and to a method for their preparation.

2. Description of the Prior Art

In the prior art, Coburn et al., *J. Org. Chem.*, 38, 3868–3871 (1973), describe the synthesis of mesoionic thiazolo[3,2-a]-s-triazine-5,7-diones, mesoionic 1,3,4-thiadiazolo[3,2-a]-s-triazine-5,7-diones, and their monothione derivatives. The reference describes in particular the synthesis of mesoionic 8-alkyl-substituted-1,3,4-thiadiazolo[3,2-a]-s-triazine-5,7-diones, which compounds differ from those of the instant application in that the reference compounds have the 8-position substituent. There is no teaching of activity for the compounds described therein. There is no suggestion that the compounds described in the instant application would be active as herbicides, or as antimicrobial agents, or as antiviral agents.

SUMMARY OF THE INVENTION

This invention relates to novel substituted thiadiazolotriazinediones which are active as herbicides and antimicrobial agents, to a novel method of preparing the substituted thiadiazolotriazinediones, and to novel herbicidal compositions and methods employing such substituted thiadiazolotriazinediones as the herbicidally-active ingredient.

DESCRIPTION OF THE PREFERRED EMBODIMENT

This invention relates to novel compounds having the formula:

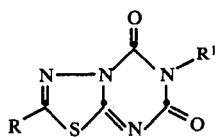

wherein

R is selected from the group consisting of methyl, chlorodifluoromethyl, difluoromethyl, trifluoromethyl, pentafluoroethyl, ti-butyl, $(CH_3)_2NSO_2$, and morpholinosulfonyl; and $R^1$ is hydrogen, methyl, ethyl, allyl, phenyl, p-nitrophenyl, or 3,5-dichlorophenyl.

Some of these novel compounds possess activity as herbicides. Thus, some of the novel compounds of this invention have shown herbicidal activity in the greenhouse when applied at rates of from about 1.12 to about 16.8 kg./ha. Therefore, this invention also relates to a novel method of controlling unwanted vegetation which comprises the application to the locus of the vegetation of an herbicidally-effective amount of a substituted thiadiazolotriazinedione.

The compounds of choice for use in the novel method of controlling unwanted vegetation are selected from the group consisting of 6-methyl-2-(trifluoromethyl)-5H-1,3,4-thiadiazolo[3,2-a]-s-triazine-5,7-(6H)-dione, 2-(dimethylsulfamoyl)-6-methyl-5H-1,3,4-thiadiazolo[3,2-a]-s-triazine-5,7-(6H)-dione, 2-(difluoromethyl)-6-methyl-5H-1,3,4-thiadiazolo[3,2-a]-s-triazine-5,7(6H)-dione, 6-methyl-2-(morpholinosulfonyl)-5H-1,3,4-thiadiazolo[3,2-a]-s-triazine-5,7(6H)-dione, and 6-ethyl-2-(trifluoromethyl)-5H-1,3,4-thiadiazolo[3,2-a]-s-triazine-5,7(6H)-dione.

The novel compounds have also variously shown activity as antiprotozoal and anti-algae agents, and as antiviral agents, as demonstrated by tests run in tissue culture against Semliki Forest virus, Maryland B virus, herpes virus, polio III virus, vaccinia virus, Rhino virus II, and echo virus at a concentration of about 2000 mcg./ml. The compounds are also variously active as antimicrobial agents at rates of from about 10 to about 100 mcg./ml. against *Staphylococcus aureus, Candida tropicalis, E. coli, Bordetella bronchiseptica, S. faecalis, Proteus morganii, Erwinia amylovora,* and *Ceratocystis ulmi.*

One of the compounds, namely 6-(3,5-dichlorophenyl)-2-(trifluoromethyl)-5H-1,3,4-thiadiazolo[3,2-a]-s-triazine-5,7(6H)-dione, is active as an aquatic growth regulator.

This invention also relates to a novel method of preparation of the claimed compounds. The novel method of preparation comprises allowing a substituted 1,3,4-thiadiazolyurea compound of the formula

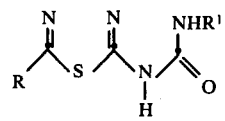

wherein

R and $R^1$ have the same significance as set forth hereinabove, to react at a suitable temperature with phosgene in a suitable solvent. Suitable solvents include methylene chloride, tetrahydrofuran, benzene, toluene, and ethyl acetate, all of which solvents are unreactive toward phosgene under the conditions used in carrying out the reaction. The solvent of choice is ethyl acetate. A suitable reaction temperature varies from about room temperature up to and including the reflux temperature of the reaction mixture. It is of course well understood by those skilled in the art that the period of time for carrying out the reaction and bringing it to substantial completion will vary inversely with the temperature at which the reaction is conducted. Thus, in carrying out the reaction in the solvent, the reaction mixture can be heated to reflux for about one-half hour and then resaturated with phosgene, after which the reaction mixture is worked up to yield the desired product. However, with the reaction temperature of choice being ambient room temperature, the reaction is run overnight, which amounts to about eighteen hours, after which the product is isolated.

The intermediate substituted 1,3,4-thiadiazolylureas are known compounds, the preparations for which are set forth in U.S. Pat. No. 3,565,901 (Feb. 23, 1971), and in U.S. Pat No. 3,726,892 (Apr. 10, 1973).

The novel method of preparation of the novel compounds of this invention is illustrated as follows: a volume of solvent is saturated with phosgene, and there is added thereto, in small portions, a quantity of a substituted 1,3,4-thiadiazolyurea, for instance 1-methyl3-[5-(trifluoromethyl)-1,3,4-thiadiazol-2-yl]urea, while continuing the introduction of phosgene into the mixture. After the addition is complete, the phosgene flow is continued for an additional period of time, suitably about a quarter of an hour, and then the reaction flask is stoppered and allowed to stir at room temperature overnight. At a higher reaction temperature, the reaction time is shorter. The crude product is recovered by filtration and recrystallized from a suitable solvent, for instance ethyl acetate, to yield, in the present example, 6-methyl-2-(trifluoromethyl)-5H-1,3,4-thiadiazolo[3,2-a]-s-triazine-5,7(6H)-dione, having a melting point of about 266°–267° C.

The following examples illustrate the preparation of the novel compounds of the invention, but are not to be construed as limiting the scope of the invention.

EXAMPLE 1

6-Methyl-2-(trifluoromethyl)-5H-1,3,4-thiadiazolo[3,2-a]-s-triazine-5,7(6H)-dione A volume of 100 ml. of ethyl acetate was saturated with phosgene, and introduction of the phosgene continued while 5.3 g. of 1-methyl-3[5-(trifluoromethyl)-1,3,4-thiadiazol-2-yl]urea was added to the solution in small portions. After the addition was complete, introduction of the phosgene was continued for an additional fifteen minutes. The flask was then stoppered and allowed to stir at room temperature overnight. The reaction product mixture was filtered and there was obtained 5.3 g. of crude solid. This crude solid was recrystallized from ethyl acetate to yield 2.3 g. (39% yield) of colorless prisms having a melting point of about 266°–267° C., and identified as 6-methyl-2-(trifluoromethyl)-5H-1,3,4-thiadiazolo[3,2-a]-s-triazine-5,7(6H)-dione.

Analyses Calc. for $C_6H_3F_3N_4O_2S$:

|   | Theoretical | Found |
|---|---|---|
| C | 28.58% | 28.87% |
| H | 1.20 | 1.28 |
| N | 22.22 | 22.35 |

Following the same general procedure of Example 1, and using appropriate starting materials, the quantities of which are indicated, the following additional compounds were prepared, and identified by elemental analyses and NMR spectra.

EXAMPLE 2

2-t-Butyl-6-methyl-5H-1,3,4-thiadiazolo[3,2-a]-s-triazine-5,7(6H)-dione, weighing 0.8 g., and having a melting point of about 163°–165° C., after recrystallization from a mixture of chloroform and hexane, from 2.1 g. of 1-[5-(t-butyl)-1,3,4-thiadiazol-2-yl]-3-methylurea and phosgene.

Analyses Calc. for $C_9H_{12}N_4O_2S$:

|   | Theoretical | Found |
|---|---|---|
| C | 44.99% | 45.20% |
| H | 5.03 | 4.87 |
| N | 23.32 | 23.11 |

EXAMPLE 3

2-(Dimethylsulfamoyl)-6-methyl-5H-1,3,4-thiadiazolo]3,2-a]-s-triazine-5,7(6H)-dione, weighing 2,3 g., and having a melting point of about 219°–221° C., from 3.8 g. of 1-(5-dimethylsulfamoyl-1,3,4-thiadiazol-2-yl)-3-methylurea and phosgene.

Analyses Calc. for $C_7H_9N_5O_4S_2$:

|   | Theoretical | Found |
|---|---|---|
| C | 28.86% | 29.14% |
| H | 3.11 | 3.11 |
| N | 24.04 | 24.24 |

EXAMPLE 4

6-Methyl-2-(morpholinosulfonyl)-5H-1,3,4-thiadiazolo]3,2-a]-s-triazine-5,7(6H)-dione, weighing 3.0 g., and having a melting point of about 230°–232° C., from 3.0 g. of 1-methyl-3-(5-morpholinosulfonyl-1,3,4-thiadiazol-2-yl)urea and phosgene.

Analyses Calc. for $C_9H_{12}N_5O_5S_2$:

|   | Theoretical | Found |
|---|---|---|
| C | 32.43% | 32.24% |
| H | 3.33 | 3.34 |
| N | 21.01 | 20.88 |

EXAMPLE 5

6-(3,5-Dichlorophenyl)-2-(trifluoromethyl)-5H1,3,4-thiadiazolo[3,2-a]-s-triazine-5,7(6H)-dione, weighing 1.5 g., and having a melting point of about 212.5-215° C., from 2.0 g. of 1-(3,5-dichlorophenyl)-3-(5-trifluoromethyl1,3,4-thiadiazol-2-yl)urea and phosgene.

Analyses Calc. for $C_{11}H_3Cl_2F_3N_4O_2S$:

|   | Theoretical | Found |
|---|---|---|
| C | 34.48% | 34.65% |
| H | 0.79 | 1.05 |
| N | 14.62 | 14.38 |

EXAMPLE 6

6-Methyl-2-(pentafluoroethyl)-5H-1,3,4-thiadiazolo[3,2-a]-s-triazine-5,7(6H)-dione, weighing 0.4 g., and having a melting point of about 250-253.5° C., from 0.6 g. of 1-methyl-3-(5-pentafluoroethyl-1,3,4-thiadiazol-2-yl)urea and phosgene.

Analyses Calc. for $C_7H_3F_5N_4O_2S$:

|   | Theoretical | Found |
|---|---|---|
| C | 27.82% | 27.66% |
| H | 1.00 | 1.07 |
| N | 18.54 | 18.66 |

EXAMPLE 7

6-Ethyl-2-(trifluoromethyl)-5H-1,3,4-thiadiazolo[3,2-a]-s-triazine-5,7-(6H)-dione weighing 1.8 g., and having a melting point of about 173°–175° C., from 1.9 g. of 1-ethyl-3-(5-trifluoromethyl-1,3,4-thiadiazol-2-yl)urea and phosgene.

Analyses Calc. for $C_7H_5F_3N_4O_2S$:

|   | Theoretical | Found |
|---|---|---|
| C | 31.58% | 31.61% |
| H | 1.89 | 1.91 |
| N | 21.05 | 21.13 |

EXAMPLE 8

2-(Difluoromethyl)-6-methyl-5H-1,3,4-thiadiazolo[3,2-a]-s-triazine-5,7(6H)-dione, weighing 1.5 g., and having a melting point of about 196°–198.5° C., from 2.0 g. of 1-methyl-3-(5-difluoromethyl-1,3,4-thiadiazol-2-yl)urea and phosgene.

Analyses Calc. for $C_6H_4F_2N_4O_2S$:

|   | Theoretical | Found |
|---|---|---|
| C | 30.77% | 31.01% |
| H | 1.72 | 1.90 |
| N | 23.92 | 23.65 |

EXAMPLE 9

2-t-Butyl-6-phenyl-5H-1,3,4-thiadiazolo[3,2-a]-s-triazine-5,7(6H)-dione, weighing 4.5 g., and having a melting point of about 221°–223° C. (sublimes), from 5.0 g. of 1-(5-t-butyl-1,3,4-thiadiazol-2-yl)-3-phenylurea and phosgene.

Analyses Calc. for $C_{14}H_{14}N_4O_2S$:

|   | Theoretical | Found |
|---|---|---|
| C | 55.61% | 55.46% |
| H | 4.67 | 4.52 |
| N | 18.53 | 18.44 |

EXAMPLE 10

2-(Trifluoromethyl)-5H-1,3,4-thiadiazolo[3,2-a]-s-triazine-5,7(6H)-dione, weighing 2.1 g., and having a melting point of about 252°–255° C., from 3.6 g. of 1-(5-trifluoromethyl-1,3,4-thiadiazol-2-yl)urea and phosgene.

Analyses Calc. for $C_5HF_3N_4O_2S$:

|   | Theoretical | Found |
|---|---|---|
| C | 25.22% | 25.04% |
| H | 0.42 | 0.31 |
| N | 23.53 | 23.70 |

EXAMPLE 11

6-(o-Tolyl)-2-(trifluoromethyl)-5H-1,3,4-thiadiazolo[3,2-a]-s-triazine-5,7-(6H)-dione, weighing 1.4 g., and having a melting point of about 178°–179° C., from 2.0 g. of 1-(o-tolyl)-3-(5-trifluoromethyl-1,3,4-thiadiazol-2-yl)urea and phosgene.

Analyses Calc. for $C_{12}H_7F_3N_4O_2S$:

|   | Theoretical | Found |
|---|---|---|
| C | 43.91% | 43.65% |
| H | 2.15 | 2.04 |
| N | 17.07 | 16.81 |

EXAMPLE 12

2-(Chlorodifluoromethyl)-6-methyl-5H-1,3,4-thiadiazolo[3,2-a]-s-triazine-5,7(6H)-dione, weighing about 1.6 g., and having a melting point of about 244°–247° C., from 2.0 g. of 1-(5-chlorodifluoromethyl-1,3,4-thiadiazol-2-yl)-3-methylurea and phosgene.

Analyses Calc. for $C_6H_3ClF_2N_4O_2S$:

|   | Theoretical | Found |
|---|---|---|
| C | 26.83% | 27.17% |
| H | 1.13 | 1.25 |
| N | 20.86 | 21.16 |

EXAMPLE 13

6-Propyl-2-(trifluoromethyl)-5H-1,3,4-thiadiazolo-[3,2-a]-s-triazine-5,7(6H)-dione, weighing 1.1 g., and having a melting point of about 134°–135° C., from 2.2 g. of 1-propyl-3-(5-trifluoromethyl-1,3,4-thiadiazol-2-yl)urea and phosgene.

Analyses Calc. for $C_8H_7F_3N_4O_2S$:

|   | Theoretical | Found |
|---|---|---|
| C | 34.29% | 34.09% |
| H | 2.52 | 2.65 |
| N | 19.99 | 19.97 |

EXAMPLE 14

6-Ethyl-2-methyl-5H-1,3,4-thiadiazolo[3,2-a]-s-triazine-5,7(6H)-dione, weighing 0.4 g., as an off-white powder, having a melting point of about 176°–184° C., from 1.8 g. of 1-ethyl-3-(5-methyl-1,3,4-thiadiazol-2-yl)urea and phosgene.

Analyses Calc. for $C_7H_8N_4O_2S$:

|   | Theoretical | Fpund |
|---|---|---|
| C | 39.62% | 39.40% |
| H | 3.80 | 3.51 |
| N | 26.40 | 26.36 |

EXAMPLE 15

6-(p-Nitrophenyl)-2-(trifluoromethyl-5H-1,3,4-thiadiazolo[3,2-a]-s-triazine-5,7(6H)-dione, weighing 0.3 g., and having a melting point of about 227°–235° C., from 2.5 g. of 1-(p-nitrophenyl)-3-(5-trifluoromethyl)-1,3,4-thiadiazol-2-yl)urea and phosgene.

Analyses Calc. for $C_{11}H_4F_3N_5O_4S$:

|   | Theoretical | Found |
|---|---|---|
| C | 36.78% | 36.79% |
| H | 1.12 | 1.31 |
| N | 19.50 | 19.44 |

EXAMPLE 16

6-Allyl-2-(chlorodifluoromethyl)-5H-1,3,4-thiadiazolo[3,2-a]-s-thiazine-5,7(6H)-dione, weighing 1.4 g., and having a melting point of about 134°–136° C., from 3.0 g. of 1-allyl-3-(5-chlorodifluoromethyl-1,3,4-thiadiazol-2-yl)urea and phosgene.

Analyses Calc. for $C_8H_6ClF_2N_4O_2S$:

|   | Theoretical | Found |
|---|---|---|
| C | 32.60% | 32.74% |
| H | 1.70 | 1.81 |
| N | 19.02 | 19.22 |

For use as herbicides, the compounds are formulated into compositions desirably containing, in addition to the substituted triazinedione, one or more of a plurality of additaments including water, polyhydroxy compounds, petroleum distillates, and other dispersion media, surface-active dispersing agents, emulsifiers, and finely-divided inert solids. The concentration of the substituted triazinedione compound in these compositions may vary depending on whether the composition is intended as an emulsifiable concentrate or a wettable powder designed to be subsequently diluted with additional inert carrier, such as water, to produce the ultimate treating composition, or is intended for direct application as a dust to plants.

Thus, treating compositions are most conveniently formulated by preparing liquid or solid concentrates, which are subsequently diluted to the desired level for use. Emulsifiable liquid concentrates can be prepared by incorporating from about 1 to about 30% by weight of the active ingredient and an emulsifying agent in a suitable water-immiscible organic liquid. Such concentrates may be further diluted with water to form spray mixtures in the form of oil-in-water emulsions. Such spray compositions then comprise active herbicide, water-immiscible solvent, emulsifying agent, and water. Suitable emulsifying agents can be of the nonionic or ionic types, or blends thereof, and include condensation products of alkylene oxides with phenols and organic acids; polyoxyethylene derivatives of sorbitan esters, such as polyoxyethylene sorbitan mono-oleate, polyoxyethylene sorbitan mono-laurate; complex ether alcohols such as polyglycol ether sulfonate; ionics of the aralkylsulfonate type, such as alkylamine dodecylbenzenesulfonate, and the like. Suitable water-immiscible organic liquids to be employed include aromatic hydrocarbons, aliphatic hydrocarbons, cycloaliphatic hydrocarbons, and mixtures thereof, such as petroleum distillates.

Solid concentrate mixtures can be prepared by incorporating from about 1 to about 90% by weight of the substituted triazinedione compound in a finely-divided inert solid carrier such as bentonite, fuller's earth, diatomaceous earth, silica, expanded mica, talc, chalk, and the like. Dispersing and/or wetting agents can be incorporated along with the substituted triazinedione in the solid carrier to form wettable powder concentrates ranging from about 1 to about 75% by weight concentration, which subsequently can be dispersed in water or other hydroxylated carrier to form spray compositions. Suitable surfactants include condensed arylsulfonic acids and sodium salts thereof, sodium lignosulfate, alkylaryl polyether alcohols, sulfonated nonionic blends, anionic wetting agents, and the like.

Spreadable granules can be prepared using calcined attapulgite clay as the solid diluent. Dry dispersion can be prepared on herbicidally-inert carriers, such as vermiculite, peat moss, and the like.

The novel compounds of this invention can be used for treating a soil area or locus infested with weed seeds with a dust, granular formulation, or spray containing one or more of the novel compounds as the herbicidally-active ingredient. Typical of soil areas which can be treated are crop growing areas in which tolerant crops are being grown; and in miscellaneous places, such as gravel driveways, clay tennis courts, walks, road shoulders, and the like where the elimination of weeds is desired. As is well understood in the art, the application rates required when the compounds are to be used in the field are greater than those mentioned above as being required in the greenhouse. In the use of the compounds in this manner on a practical basis, compositions containing the herbicidally-active compound can be sprayed, dusted, or spread by methods well known to the art onto the particular area at the rate of around 1.12 kg./ha. to about 36 kg./ha., suitably from about 2.24 to about 22.4 kg./ha., or somewhat more if necessary, for example, 56 kg. of active ingredient per hectare.

As pointed out above, the novel compounds of this invention are active as herbicides, mainly as preemergent herbicides. The herbicidal activity has been established by tests which have been carried out as described hereinafter.

TEST 1

A soil was prepared consisting of 1 part masonry sand and 1 part shredded topsoil blended together and then sterilized in an autoclave at approximately 118° C. for about 24 hours. Postemergence and preemergence plantings were made in plastic containers which measured 6.7 cm. on a side at the top, 5.4 cm. on a side at the bottom, and having a height of 5.9 cm. Each container had four bottom holes for drainage. Each container was filled with 150 ml. of the standard soil mixture and the soil in the container was tamped and leveled with a bench brush. The seeds were planted in individual rows. Depending upon germination, 6 to 12 tomato seeds (*Lycopersicon esculentum*) were planted in the middle row. In one side row there were planted 75 to 125 large crabgrass seeds (*Digitaria sanguinalis*). In the other side row there were planted 50 to 100 pigweed seeds (*Amaranthus retroflexus*). Twenty ml. of the soil mixture was then added to the container to cover the seeds.

Approximately 30 ml. of a fertilizer solution containing 158 mg. of a soluble fertilizer (23-21-17) was added to each container four days before treatment.

The postemergence containers were planted 11 to 13 days prior to treatment and given 12 to 18 hours of light each day, depending upon the environment conditions, and subjected to a temperature of about 23° to about 27° C. The preemergence containers were planted the day prior to treatment. After treatment, all of the containers were moved into a greenhouse.

The compounds studied in this test were applied at the rate of 16.8 kg./ha. The formulation for an application rate of 16.8 kg./ha. was accomplished by dissolving 20 mg. of the test compound in about 1 ml. of a solvent containing acetone and ethyl alcohol in a 1:1 ratio, together with a small amount of Toximul R and S. This solution containing the compound was diluted to 4 ml. with deionized water. Toximul R and Toximul S are sulfonate/nonionic blends which are products of Stepan Chemical Company, Northfield, Ill.

The herbicidal compositions were applied to each container with a greenhouse DeVilbiss atomizer hooked to an air source. In the preemergent tests, the herbicidal compositions were sprayed on the surface of the coil in the flat after the seeds were planted. In the postemergent tests, the herbicidal compositions were sprayed on the foliage of the plants 11–13 days after planting the seeds from which the plants grew. One and one-half ml. of the composition under test was applied to each container. This is equal to a 16.8 kg./ha. application rate. One pre- and one postemergence container was treated at this rate for each compound.

After treatment, all the containers were transferred to the greehouse and watered as necessary for 10 to 13 days after treatment, depending upon the season. Herbicidal effects were then rated on each plant species. The ratings were based on a 1 to 5 scale:

1 = no injury

2 = slight injury
3 = moderate injury
4 = severe injury
5 = death

Table 1, which follows, sets forth the results of the testing of some of the compounds. In the table, column 1 identifies the compound by its operating example number in the specification; columm 2, the rate in terms of kg./ha. at which the compound was applied to the test containers; and columns 3 to 8, the injury rating for particular plant seedlings.

The test plants are identified by letters of the alphabet, as set forth hereinbelow:

A — Tomato
B — Large Crabgrass
C — Pigweed

Table 1

| Compound | Appln. Rate kg./ha. | Plant Injury Ratings | | | | | |
|---|---|---|---|---|---|---|---|
| | | Preemergence | | | Postemergence | | |
| | | A | B | C | A | B | C |
| 4 | 16.8 | 2 | 3 | 5 | 2 | 2 | 4 |
| 6 | 16.8 | 4 | 4 | 5 | 5 | 5 | 5 |
| 7 | 16.8 | 1 | 2 | 2 | 4 | 2 | 5 |

TEST 2

The soil used in this test was prepared by blending together one part masonry sand and one part shredded topsoil. Plantings were made in the soil contained in galvanized metal flats which measured 31.5 cm. long, 21.5 cm. wide, and 8 cm. deep, with holes and grooves in the bottom for drainage. Each flat was filled two-thirds full with soil and the soil was leveled and tamped. All the seeds were planted in rows perpendicular to the long axis of the flat, one species per row. The large seeds of morningglory and corn were planted in rows and 1 cm. deep made by a hand-held press. The remainder of the seeds, that is, the small seeds, were planted by sprinkling the seeds in rows on the surface of the prepared soil in the trays, and then all of the seeds were covered with from 0.5 cm. to 1.0 cm. of sifted soil. The approximate number of seeds planted per species and the species are as follows:

A — Corn (Zea mays) 4
B — Large crabgrass (Digitaria sanguinalis) 350
C — Pigweed (Amaranthus retroflexus) 350
D — Foxtail millet (Setaria italica) 200
E — Velvetleaf (Abutilon theophrasti) 100
F — Morningglory (Ipomoea purpurea) 25
G — Zinnia (Zinnia elegans) 20

Two and one-half g. of soluble fertilizer was applied to each flat during the first watering after planting. The postemergence flats were plantes 10-13 days prior to treatment and were then placed in a growth chamber until the day of treatment. The flats were given 12-18 hours of light each day, depending on light intensity, and subjected to a temperature of 23°-27° C. The preemergence flats were planted the same day the treatments were applied. After treatment, all the flats were moved into a greenhouse.

The compounds studied in this test were applied at the rate of 8.96 kg./ha. The formulation for an application rate of 8.96 kg./ha. was accomplished by dissolving 120 mg. of the test compound in 2.5 ml. of a solvent containing acetone and ethyl alcohol in a 1:1 ratio together with a small amount of Toximul R and S. The solution was then diluted with deionized water to a volume of 25 ml.

The herbicidal compositions were applied to each flat with a modified DeVilbiss atomizer hooked to an air source. In the preemergent test, the herbicidal compositions were sprayed on the surface of the soil in the flat after the seeds were planted. In the postemergent test, the herbicidal compositions were sprayed on the foliage of the plants 10-13 days after planting the seeds from which the plants grew. Twelve and one-half ml. of the composition under test was applied to each flat. This is equal to an 8.96 kg./ha. application rate.

After treatment, all the flats were transferred to the greenhouse for 12-13 days. Herbicidal effects were then rated on each plant species. The ratings were based on a 1 to 5 scale as described in Test 1.

Table 2, which follows, sets forth the results of the testing of the compounds. In the table, column 1 identifies the compound by its operating example number in the specification; column 2, the rate in terms of kg./ha. at which the compound was applied to the test flat; columns 3 to 9, the injury rating for particular plant seedlings. The test plants are identified by letters of the alphabet, as set forth hereinabove:

Table 2

| Comp. | Appln. Rate kg./ha. | Plant Injury Ratings | | | | | | | | | | | | |
|---|---|---|---|---|---|---|---|---|---|---|---|---|---|---|
| | | Preemergence | | | | | | | Postemergence | | | | | |
| | | A | B | C | D | E | F | G | A | B | C | D | E | F | G |
| 1 | 8.96 | 1 | 4 | 5 | 2 | 2 | 1 | 2 | 1 | 1 | 2 | 2 | 2 | 1 | 3 |
| 3 | 8.96 | 2 | 4 | 5 | 4 | 3 | 1 | 3 | 1 | 2 | 2 | 4 | 2 | 1 | 1 |
| 6 | 8.96 | 2 | 3 | 5 | 3 | 5 | 1 | 4 | 1 | 3 | 3 | 3 | 3 | 1 | 3 |
| 8 | 8.96 | 3 | 4 | 4 | 2 | 5 | 2 | 4 | 1 | 3 | 4 | 2 | 3 | 2 | 3 |

TEST 3

Further testing of certain of the compounds falling within the scope of the above generic formula as preemergent herbicides was carried out against a broader spectrum of plants. The plant species used in this experiment were planted in galvanized pans exactly like those used in Test 2, using the same type of soil. Each flat was filled two-thirds full with the prepared soil and the soil leveled and tamped. In these preemergence tests, two flats containing ten indicator species each were used for each application rate of each chemical. The seeds of the species of plants were planted in rows parallel to the long axis of the flat, one species per half row, in the same manner as in Test 2. The approximate numbers of seeds planted are as follows:

A — Corn (Zea mays) 4
B — Cotton (Gossypium hirsutum) 6
C — Soybean (Glycine max) 6
D — Wheat (Triticum aesitivum) 40
E — Alfalfa (Medicago sativa) 100
F — Sugarbeet (Beta vulgaris) 25
G — Rice (Oryza sativa) 46
H — Cucumber (Cucumis sativus) 8
I — Tomato (Lycopersicon esculentum) 30
J — Barnyardgrass (Echinochloa crus-galli) 50

K — Lambsquarter (*Chenopodium album*) 100
L — Large crabgrass (*Digitaria sanguinalis*) 100
M — Mustard (*Brassica juncea*) 50
N — Pigweed (*Amaranthus retroflexus*) 150
O — Foxtail millet (*Setaria italica*) 100
P — Wild oat (*Avena fatua*) 25
Q — Velvetleaf (*Abutilon theophrasti*) 25
R — Jimsonweed (*Datura stramonium*)
S — Morningglory (*Ipomoea purpurea*) 15
T — Zinnia (*Zinnia elegans*) 20

For this preemergence testing, the flats were planted the same day as the treatments were applied, and the seeds were covered with 0.5 to 1.0 cm. of soil. The chemicals were formulated the same way as described in Test 2, and then serially diluted to provide the desired concentrations of test solutions for applications at the desired rate. Chemicals were applied to the surface of the flats using a modified DeVilbiss atomizer connected to an air source. Each flat received 12.5 ml. of spray solution. The flats were maintained in the greenhouse after the treatment.

The herbicidal effects of the chemicals were evaluated about 18–21 days after preemergence applications. The degree of plant injury is based on a 1 to 5 scale (as in Tests 1 and 2), and a single numerical rating was assigned to each plant species.

Table 3, which follows, sets forth the results of the preemergent testing of the compounds against crops, grasses, and broadleaf weeds. In the table, column 1 identifies the compound; column 2, the rate in terms of kg./ha. at which the compound was applied to the test flat; and the remainder of the columns, the injury rating for the particular plant seedlings.

TABLE 3

| Compound | Appln. Rate kg./ha. | Preemergence Plant Injury Ratings | | | | | | | | | | | | | | | | | | |
|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| 3 | 1.12 | 1 | 1 | 1 | 1 | 3 | 2 | 1 | 1 | 1 | 1 | 4 | 2 | 2 | — | 2 | 2 | 2 | 2 | 1 | 3 |
| | 2.24 | 1 | 1 | 1 | 2 | 4 | 4 | 1 | 3 | 2 | 5 | 5 | 4 | 5 | — | 3 | 2 | 4 | 4 | 1 | 5 |
| | 4.48 | 2 | 1 | 1 | 2 | 5 | 4 | 2 | 2 | 2 | 5 | 4 | 4 | 2 | — | 5 | 3 | 2 | 2 | 1 | 5 |
| 8 | 1.12 | 1 | 1 | 1 | 2 | 3 | 3 | 2 | 3 | 3 | 2 | 3 | 2 | 2 | 1 | 2 | 2 | 3 | 3 | 1 | 3 |
| | 2.24 | 1 | 1 | 2 | 2 | 3 | 5 | 3 | 5 | 4 | 2 | 5 | 4 | 2 | 1 | 5 | 3 | 5 | 4 | 2 | 4 |
| | 4.48 | 2 | 2 | 2 | 3 | 5 | 5 | 3 | 5 | 5 | 3 | 5 | 5 | 4 | 3 | 2 | 5 | 5 | 4 | 3 | 5 |

The results appearing in the tables show that the compounds are most active as preemergent herbicides.

I claim:

1. A compound of the formula

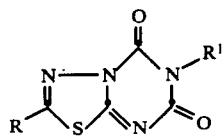

wherein
R is selected from the group consisting of methyl, chlorodifluoromethyl, difluoromethyl, trifluoromethyl, pentafluoroethyl, t-butyl, (CH$_3$)$_2$NSO$_2$, and morpholinosulfonyl; and R$^1$ is hydrogen, methyl, ethyl, allyl, phenyl, p-nitrophenyl, or 3,5-dichlorophenyl.

2. A compound as in claim 1, said compound being 6-methyl-2-(trifluoromethyl)-5H-1,3,4-thiadiazolo[3,2-a]-s-triazine-5,7(6H)-dione.

3. A compound as in claim 1 said compound being 2-t-butyl-6-methyl-5H-1,3,4-thiadiazolo-[3,2-a]-s-triazine-5,7(6H)-dione.

4. A compound as in claim 1, said compound being 2-(difluoromethyl)-6-methyl-5H-1,3,4-thiadiazolo[3,2-a]-s-triazine-5,7(6H)-dione.

5. A compound as in claim 1, said compound being 2-(dimethylsulfamoyl)-6-methyl-5H-1,3,4-thiadiazolo[3,2-a]-s-triazine-5,7(6H)-dione.

6. 6-Methyl-2-(pentafluoroethyl)-5H-1,3,4-thiadiazolo[3,2-a]-s-triazine-5,7(6H)-dione.

7. A method of controlling unwanted vegetation which comprises the application to the locus of the vegetation of an herbicidally-effective amount of a compound selected from the group consisting of 6-methyl-2-(trifluoromethyl)-5H-1,3,4-thiadiazolo[3,2-a]-s-triazine-5,7(6H)-dione, 2-(dimethylsulfamoyl)-6-methyl-5H-1,3,4-thiadiazolo[3,2-a]-s-triazine-5,7(6H)-dione, 2-(difluoromethyl)-6-methyl-5H-1,3,4-thiadiazolo[3,2-a]-s-triazine-5,7(6H)-dione, 6-methyl-2-(morpholinosulfonyl)-5H-1,3,4-thiadiazolo[3,2-a]-s-triazine-5,7(6H)-dione, and 6-ethyl-2-(trifluoromethyl)-5H-1,3,4-thiadiazolo[3,2-a]-s-triazine-5,7(6H)-dione.

8. The method of claim 6 wherein the herbicidal compound is applied at the rate of from about 1.12 to about 56 kg./ha.

9. The method of claim 6 wherein the herbicidal compound is applied at the rate of from about 2.24 to about 22.4 kg./ha.

10. The method of claim 6 wherein the herbicidal compound is 2-(dimethylsulfamoyl)-6-methyl-5H-1,3,4-thiadiazolo[3,2-s]-s-triazine-5,7(6H)-dione.

11. The method of preparing a compound as defined in claim 1 which comprises allowing a compound of the formula

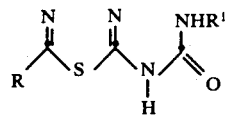

wherein
R and R$^1$ have the same significance as in claim 1, to react with phosgene in solvent, and isolating the product.

12. The method of claim 11 wherein the solvent is ethyl acetate.

* * * * *

UNITED STATES PATENT OFFICE
CERTIFICATE OF CORRECTION

Patent No. 4,042,372            Dated   August 16, 1977

Inventor(s)  Richard W. Harper

It is certified that error appears in the above-identified patent and that said Letters Patent are hereby corrected as shown below:

Column 2, line 26:  The structure should appear as follows:

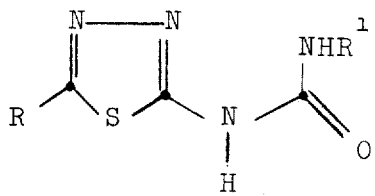

Column 2, line 63:  "methyl3" should read --methyl-3--.

Column 3, line 64:  "2,3" should read --2.3--.

Column 4, line 12:  "$\overline{3}$,2" should read --$\underline{3}$,2--.

Column 4, line 30:  "thyll" should read --thyl-1--.

Column 5, line 51:  "179°C" should read --179.5°C--.

Column 6, line 54:  "thiazine" should read --triazine--.

Column 7, line 51:  "dispersion" should read --dispersions--.

Column 8, line 52:  "greenhouse" should read --modified--.

UNITED STATES PATENT OFFICE
CERTIFICATE OF CORRECTION

Patent No. 4,042,372　　　　　　　　Dated August 16, 1977

Inventor(s) Richard W. Harper

It is certified that error appears in the above-identified patent and that said Letters Patent are hereby corrected as shown below:

Column 8, line 64: "greehouse" should read --greenhouse--.

Column 9, line 63: "plantes" should read --planted--.

Column 12, line 53: The structure should appear as follows:

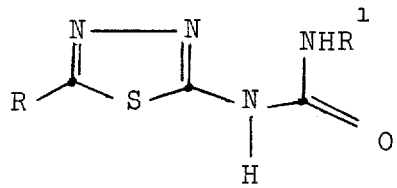

Signed and Sealed this

Twenty-first Day of February 1978

[SEAL]

Attest:

RUTH C. MASON　　　　　　LUTRELLE F. PARKER
Attesting Officer　　Acting Commissioner of Patents and Trademarks